United States Patent [19]

Kasahara et al.

[11] 4,407,944

[45] * Oct. 4, 1983

[54] METHOD FOR DETERMINING THE ACTIVITY OF THE ANGIOTENSIN-CONVERTING ENZYME

[75] Inventors: Yasushi Kasahara, Tama; Yoshihiro Ashihara, Fuchu, both of Japan

[73] Assignee: Fujizoki Pharmaceutical Co., Ltd., Tokyo, Japan

[*] Notice: The portion of the term of this patent subsequent to Sep. 29, 1998 has been disclaimed.

[21] Appl. No.: 330,110

[22] Filed: Dec. 14, 1981

[30] Foreign Application Priority Data

Dec. 23, 1980 [JP] Japan .................. 55-181307

[51] Int. Cl.³ .................. C12Q 1/34; C12Q 1/36
[52] U.S. Cl. .................. 435/18; 435/24
[58] Field of Search .................. 435/23, 24, 13, 18, 435/19, 4

[56] References Cited

U.S. PATENT DOCUMENTS 4,115,374  9/1978  Ryan et al. .................. 435/23
4,260,682  4/1981  Ryan et al. .................. 435/24
4,292,404  9/1981  Kasahara et al. .................. 435/24

Primary Examiner—Esther M. Kepplinger
Attorney, Agent, or Firm—Flynn, Thiel, Boutell & Tanis

[57] ABSTRACT

A method for determining the activity of an angiotensin-converting enzyme is disclosed comprising the steps of mixing a liquid containing (i) a synthetic substrate X-hippuryl-L-dipeptide having the formula

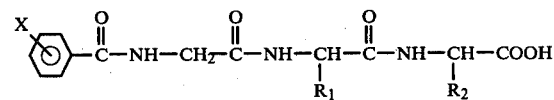

wherein X represents OH, $NH_2$ or $N(CH_3)_2$, and when $R_1$ is H, $R_2$ is H, and when $R_1$ is

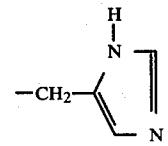

$R_2$ is $CH_2CH(CH_3)_2$, (ii) hippuricase and (iii) 4-aminoantipyrine, with a liquid containing an angiotensin-converting enzyme; measuring colorimetrically the concentration of the quinonimine dye which is formed by adding an oxiding agent to the above mixture; and calculating the activity of the angiotensin-converting enzyme from the concentration of the quinonimine dye.

4 Claims, No Drawings

METHOD FOR DETERMINING THE ACTIVITY OF THE ANGIOTENSIN-CONVERTING ENZYME

BACKGROUND OF THE INVENTION

The present invention relates to a method for determining the activity of the angiotensin-converting enzyme, and more particularly to a method for determining the activity of the angiotensin-converting enzyme comprising the steps of mixing a liquid containing (i) a synthetic substrate of X-hippuryl-L-dipeptide having the formula

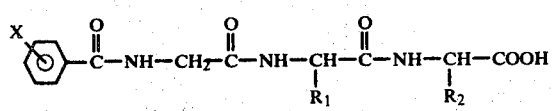

wherein X is OH, $NH_2$ or $N(CH_3)_2$, and wherein the pair of substituents ($R_1$, $R_2$) is either (a). (H,H), or (b).

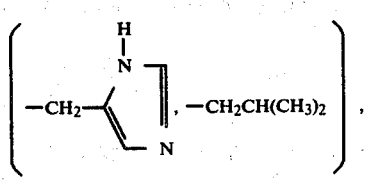

(ii) hippuricase and (iii) 4-aminoantipyrine, with a liquid containing angiotensin converting enzyme, and measuring colorimetrically the concentration of a quinonimine dye which is formed by adding an oxidizing agent to the above mixture.

The angiotensin-converting enzyme (hereinafter referred to as ACE) acts on angiotensin I in the human body and liberates a C-terminal dipeptide (i.e., L-histidyl-L-leucine) from angiotensin I, so that an active type angiotensin II that has the effect of increasing blood pressure is produced. ACE plays an important role in the human body in collaboration with a renin-angiotensin enzyme group or with a quinine-kallikrein enzyme group. Furthermore, by checking the level of the ACE in the blood, diagnosis of sarcoidosis can be performed. Therefore, the measurement of the enzyme activity of ACE is meaningful physiologically and clinically.

The following methods of measuring the enzyme activity of ACE have been proposed:

(1) a method employing a radioisotope, (2) a method employing a fluorescent material, and (3) a method employing liquid chromatography. All of these methods, however, require special equipment.

In addition to the above-mentioned methods, a method proposed by Cushman et al is known. In this method, the synthetic substrate hippuryl-L-histidyl-L-leucine is allowed to react with a test sample containing ACE, for instance, with serum or body fluid, for a predetermined period of time to produce hippuric acid, and then hydrochloric acid is added to the reaction mixture to terminate the reaction. The hippuric acid thus produced is extracted with ethyl acetate. Ethyl acetate is then evaporated from the extracted solution, leaving a dried solid. The dried solid is dissolved in distilled water and the absorbence of the solution is determined in the ultraviolet region, so that the concentration of hippuric acid is determined and, from the concentration of hippuric acid, the activity of ACE is calculated. This method entails complicated steps and, therefore, is not always practical.

SUMMARY OF THE INVENTION

It is, therefore, an object of the present invention to provide a method for determining the activity of angiotensin-converting enzyme (ACE) which method is improved with respect to accuracy of measurement and cost, and which, unlike the conventional methods, does not require complicated measurement steps.

According to the present invention, a test reagent comprising (i) the synthetic substrate X-hippuryl-L-dipeptide, as defined above, (ii) hippuricase, (III) 4-aminoantipyrine, and (iv) an oxidizing agent, for example, periodic acid, perchloric acid, potassium ferricyanide, ammonium ceric nitrate, chloramine T, chloramine B or chromium trioxide, is mixed with a liquid containing ACE. A quinonimine dye is formed by mixing the test reagent with the ACE-containing liquid. The concentration of the quinonimine dye is then colorimetrically measured, whereby the activity of the ACE is determined.

The key feature of the present invention is that the activity of the ACE can be determined more accurately and inexpensively in comparison with the conventional methods, because the oxidizing agents which can be employed in the present invention are stable in their properties and inexpensive.

DETAILED DESCRIPTION OF THE PREFERRED EMBODIMENT

The procedure of the method for determining the activity of ACE according to the present invention will be explained below.

X-hippuryl-L-dipeptide is added to a liquid containing ACE, for instance, serum or body fluid. As a result, X-hippuric acid and L-dipeptide are formed. To this mixture hippuricase is added so that X-benzoic acid and glycine are formed. X-benzoic acid is oxidized by the oxidizing agent, in the presence of 4-aminoantipyrine, and is condensed with 4-aminoantipyrine to form a quinonimine dye. The concentration of the quinonimine dye is colorimetrically measured and, from the concentration of the quinonimine dye, the activity of ACE is calculated.

The principle of the present invention can be summarized by the following equations:

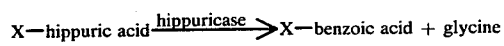

quinonimine dye

In the present invention, as the synthetic substrate X-hippuryl-L-dipeptide, p-hydoxyhippurylglycyl-glycine having the formula

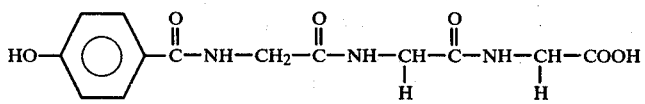

and p-hydroxyhippuryl-L-histidyl-L-leucine having the formula

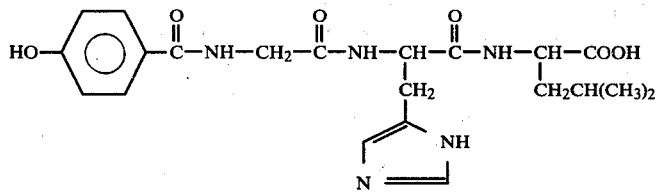

are particularly useful, and as the oxidizing agent, periodic acid is particularly useful.

EXAMPLE

To 0.5 ml of a test reagent containing 5.6 mM of p-hydroxyhippuryl-L-histidyl-L-leucine, 1 U of hippuricase, 2 mM of 4-aminoantipyrine, 0.5 M of sodium chloride and 0.1 M of boric acid, was added 50 μl of serum. The mixture was allowed to react at 37° C. for 20 minutes. To this reaction mixture was added 0.5 ml of a reaction termination solution containing 3 mM of ethylenediaminetetraacetic acid (EDTA) and 17.5 mM of sodium periodate. The mixture was maintained at 37° for 5 minutes, so that quinonimine dye was formed. The absorbance of the reaction mixture was measured at a light wavelength of 505 nm, which is referred to as Absorbance A.

Separately, a reagent for a blank (comparison) test was prepared by adding 0.5 ml of a solution containing 0.1 M of boric acid to 0.5 ml of the reaction termination solution, followed by addition of 0.05 ml of serum to the reaction mixture.

In the same manner as described above, the absorbance of the blank test reagent was measured at a light wavelength of 505 nm, which is referred to as Absorbance B.

The activity unit (mU) of ACE can be calculated by the following equation:

$$mU = \frac{A-B}{\text{Molecular extinction coefficient }(\epsilon)} \times \frac{1}{\text{Reaction time (20 min.)}} \times \frac{1}{\text{Light path length (cm)}} \times \frac{1.05}{0.05} \times 10^6$$

where $\epsilon = 12\ 000$ (Molecular extinction coefficient of quinonimine dye)

By repeating the above-described test 20 times, the following results was obtained:

Activity unit (mU) = 20 ± 0.3 (nmol/ml/min)
Coefficient of variation (CV) = 1.5%

The subject matter of the present invention is related to the subject matter of U.S. Pat. No. 4,292,404, the entire contents of which are incorporated herein by reference.

What is claimed is:

1. A method for determining the activity of angiotensin-converting enzyme comprising the steps of:
    (1) mixing a liquid containing (i) X-hippuryl-L-dipeptide having the formula

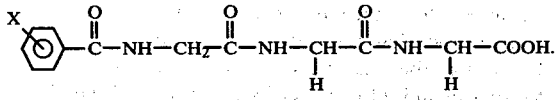

wherein X is OH, $NH_2$ or $N(CH_3)_2$, and wherein the pair of substituents ($R_1$, $R_2$) is (a). (H, H,) or (b).

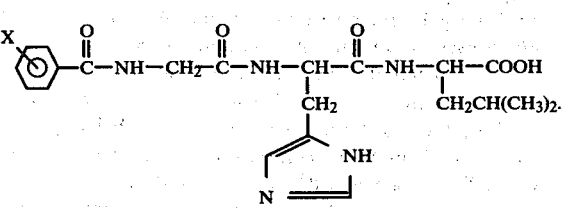

(ii) hippuricase and (iii) 4-aminoantipyrine, with a liquid containing said angiotensin-converting enzyme to form a reaction mixture;
    (2) adding an oxidizing agent to said reaction mixture under reaction conditions effective to form quinonimine dye, and
    (3) colorimetrically measuring the concentration of said quinonimine dye.

2. A method according to claim 1, wherein said X-hippuryl-L-dipeptide is X-hippuryl-glycyl-glycine having the formula 3. A method according to claim 1, wherein said X-hippuryl-L-dipeptide is X-hippuryl-L-histidyl-L-leucine which is represented by the formula 4. A method according to claim 1, claim 2 or claim 3 wherein said oxidizing agent is one member selected from the group consisting of periodic acid, perchloric acid, potassium fericyanide, ammonium ceric nitrate, chloramine-T, chloramine-B and chromium trioxide.

* * * * *